United States Patent [19]
Holowko et al.

[11] Patent Number: 6,039,251
[45] Date of Patent: Mar. 21, 2000

[54] METHOD AND SYSTEM FOR SECURE CONTROL OF A MEDICAL DEVICE

[76] Inventors: Paul L. Holowko, 1300 Chisolm Trail; Aaron D. Crone, 9088 Wood Stream La., both of Dayton, Ohio 45458

[21] Appl. No.: 09/061,444

[22] Filed: Apr. 16, 1998

[51] Int. Cl.$^7$ .................................................. G06K 5/00
[52] U.S. Cl. ........................................... 235/380; 235/375
[58] Field of Search ................................. 235/380, 375, 235/376, 382, 382.5, 437, 492

[56] References Cited

U.S. PATENT DOCUMENTS

| | | | |
|---|---|---|---|
| 3,917,045 | 11/1975 | Williams et al. | 194/4 C |
| 4,491,725 | 1/1985 | Pritchard | 705/2 |
| 4,831,245 | 5/1989 | Ogasawara | 235/492 |
| 4,857,716 | 8/1989 | Gombrich | 235/375 |
| 4,953,745 | 9/1990 | Rowlett, Jr. | 235/381 |
| 5,291,399 | 3/1994 | Chaco | 235/375 |
| 5,338,157 | 8/1994 | Blomquist | 417/2 |
| 5,412,564 | 5/1995 | Ecer | 600/300 |
| 5,487,161 | 1/1996 | Koenck et al. | 395/442 |
| 5,500,517 | 3/1996 | Cagliostro | 235/486 |
| 5,550,359 | 8/1996 | Bennett | 235/382 |
| 5,594,786 | 1/1997 | Chaco | 379/93.09 |
| 5,602,915 | 2/1997 | Campana | 380/21 |
| 5,629,508 | 5/1997 | Findley, Jr. | 235/382 |
| 5,717,433 | 2/1998 | Doba | 345/173 |

OTHER PUBLICATIONS

I–Flow Corp., Printout from I–Flow Corp. website, www.i-flowcorp.com, 1998, pages "/frmain.html", "/electronics.html", "/freedemo.html", "/company_information.html", "/faq1.html", "/support_main.html".

*Primary Examiner*—Michael G Lee
*Assistant Examiner*—Diane I. Lee
*Attorney, Agent, or Firm*—Dinsmore & Shohl LLP

[57] ABSTRACT

A method and system for controlling an in-home medical device, such as a drug delivery pump, wherein a control program or "prescription" for control of the device is encoded on a portable card, such as a smartcard. Accordingly, the card can be used on other medical devices without the need to reprogram the devices. In addition, the medical device is monitored and data relating to the device can be saved to the smartcard so that a paperless and portable record can be kept of the device operation. In the case of a drug delivery pump, the prescription dictates the rate of drug delivery, the frequency of drug delivery, and other variables associated with the treatment being provided. In addition, a security program is provided which ensures that only authorized patients can utilize the medical device. The program compares an access code stored on the patient card with an access code stored in the device memory and allows the device to operate if the codes match. Moreover, remote access to the medical device is provided through a communication system between the controller for the medical device and a remotely located computer. Information can be downloaded to the computer over the communication system and the prescription on the portable card can be edited as needed. Additional security is provided by utilizing a second card reader at the remote location for reading a provider identification code from a second card. If the provider code does not match a code on the first card, communication between the controllers is prevented.

9 Claims, 5 Drawing Sheets

METHOD AND SYSTEM FOR SECURE CONTROL OF A MEDICAL DEVICE

TECHNICAL FIELD

The present invention relates to drug delivery systems and methods, and, more particularly, to drug delivery dispensers which can be controlled from a remote location and which can be used with smartcard systems for secure control of the dispensers and for efficiently acquiring data relating to the dispenser operation.

BACKGROUND OF THE INVENTION

Today, many patients recovering from operations or suffering from medical ailments, are permitted (or required) to complete their recovery or undergo medical treatment at home, thereby providing a more comfortable environment for the patient and reducing the cost of the treatment. This trend has also led to the increase in the use of home health care equipment for facilitating in the patient's recovery. This equipment can include oxygen and oxygen delivery systems as well as ambulatory pumping and other dispensing devices for delivering prescription medicines and other substances.

While such home health care recovery and rehabilitation programs can save money and have other advantages, they had a disadvantage in that the health care provider was required to make a trip to the home of the patient in order to monitor and/or change the operation of the home health care device, or to gather data regarding the operation of the device. For example, if the prescription for the patient was to be changed, the health care provider needed to physically travel to the home of the patient and reprogram the drug delivery dispenser.

Accordingly, systems have been developed which allow for the remote access by the health care provider to the in-home health care device, and which thereby allow the health care provider to interrogate, monitor and/or program the device from a location which is remote with respect to the patient's home (e.g., a health care facility). These programs also allow the provider to monitor the operation of the pump from this remote location. For example, the VERIFUSE PLUS™ delivery system with the VOICE LINK® communications feature, marketed by the I-Flow Corporation, allows the health care provider to communicate with a pump from anywhere using a touch tone telephone. The voice communication software resides in the patient's pump and guides the health care provider through the programming steps via a voice mail system. The system also allows the health care provider to diagnose an alarm status from a remote location, as well as to change existing programs for the medical equipment.

U.S. Pat. No. 5,338,157, issued to Blomquist, discloses another system and method for communicating with transportable medical devices, and in particular, with drug pumps. In one embodiment, a communication system is provided where a remote drug pump communicates with a similar local drug pump over telephone communication lines, such as through modems, for example. Each of the drug pumps are provided with a pump controller for controlling the operation of the pump, and the controller may include a processor and associated memory for storing operating programs and other information. Each drug pump can include an operator input mechanism for making inputs to the controller, as well as a display mechanism for displaying information about operations of the pump. When communication has been established between the pumps, the caregiver pump can be used by the caregiver for data gathering, trouble shooting, and operational program changes with respect to the remote patient pump. In another embodiment, the controller for the pump is put into a "locked" status through an access code program which prevents the patient from altering the pump operations program or from accessing other pump information in the memory.

While the device disclosed in this patent provides some security for preventing the patient from altering the patient pump program, the security means disclosed lacks certain capabilities. For example, no security mechanism is provided in the patent for ensuring that only the appropriate patient can use the remote medical equipment. Thus, an unauthorized individual can apparently begin use of the remote medical equipment and thereby damage the equipment, or injure themselves or the patient. Moreover, the patent does not describe a means for ensuring that only those particular caregivers who are in charge of the particular patient are permitted to communicate with the patient's remote medical equipment. Thus, an unauthorized caregiver in the caregiver facility might sign on and accidentally or intentionally change the remote pump program thereby endangering the patient. Moreover, this individual might gain unauthorized access to personal data regarding the patient or their medical device.

In addition, the devices described above do not provide means for saving the operation program (i.e., the "prescription") and historical operation data for the medical device in a convenient and portable form, such that the patient can easily transport the program with them for use at other locations or health care facilities. While prior art devices can be reprogrammed with new prescription programs for use with a different patient, such a reprogramming process can be time consuming and requires knowledge of the functions and structure of the particular device being reprogrammed.

Moreover, the systems and devices of the prior art do not provide a means for monitoring the operation of the medical device and saving the data regarding these operations in a convenient and portable medium. While prior art devices allow such data to be collected and saved, the data has not been provided on a medium that can easily and safely be carried by the patient, such as might fit in the patient's wallet, so that the patient may keep the data on his or her person at all times.

Accordingly, to overcome the above and other problems, it is desirable to provide portable medical devices that are operated in a secure manner, such that only authorized patients can use the device. In addition, it is desirable to allow remote control access to such devices in a controlled and secure manner, such that only those care providers treating the patient can access the data and programs associated with the device. Moreover, it is desirable to provide the control programs and data associated with such devices in a convenient and portable format, such that the programs and data can be easily transferred from one device to another, without the need for extensive reprogramming. Moreover, it is desirable to provide a paperless recording system for recording the operational data associated with in-home medical devices in a format that can be easily kept with the patient at all times.

SUMMARY OF THE INVENTION

Accordingly, it is an object of the present invention to obviate the above-described problems.

It is another object of the present invention to provide a system and method for remote data acquisition and control of an in-home medical device.

Another object of the present invention is to provide a system and method for communication with remote medical equipment that allows only authorized caregivers to access the remote medical equipment.

Another object of the present invention is to provide a system and method for controlling in-home medical equipment which ensures that only authorized patients can make use of the equipment.

Another object of the invention is to reduce the amount of time and expense required in reprogramming a portable medical device for use with another patient.

Yet another object of the invention is to provide control programs for in-home medical devices which are in an easily transportable format, such that the program can be quickly and easily transferred to a different device at a different location.

It is another object of the present invention to provide improved data monitoring and handling capabilities for monitoring the operation of remote medical equipment.

Another object of the present invention is to provide a system and method for saving data regarding portable medical equipment which allows the data to be saved at the patient location and in a form which can be easily carried by the patient.

Additional objects, advantages, and other novel features of this invention will be set forth in part in the description that follows.

To achieve the foregoing and other objects, and in accordance with the purposes of the present invention as described above, a system for controlling a medical device is provided. The system includes a medical device for use in medical treatment at a remote location and which is controllable by control instructions. The system also includes a first portable card having control instructions encoded thereon, a first card reader for receiving the first portable card and for reading the control instructions from the first card, and a control device in communication with the first card reader and the medical device. The control device includes a control program for receiving the control instructions from the first card and applying the instructions to the medical device for control thereof.

In a further aspect of the invention, a system for secure operation of a medical device is provided, comprising a medical device for use in medical treatment at a remote location and which is controllable by control instructions. The system also includes a first portable card having a first code and control instructions encoded thereon, a first card reader for receiving the first portable card and for reading the first code and control instructions from the first card, and a first control device in communication with the first card reader and the medical device. The first control device includes a control program for applying the control instructions to the medical device for control thereof. The system also includes a second control device located a distance from the remote location, a second portable card having a second code encoded thereon, and a second card reader connected to the second control device for receiving the second card. The system further includes a communication system for allowing communication between the first control device and the second control device. The second control device is configured to download the control instructions from the first card through the communication system and to allow editing of the downloaded instructions. Also provided is a first security mechanism in communication with the card readers for receiving the first and second codes from the cards. The first security mechanism is configured to determine whether the codes are compatible and to prevent the editing of the control instructions if the codes are not compatible.

In a further aspect of the invention, a method for securely controlling a medical device using a smartcard and a smartcard reader is also provided. The method comprises reading a first equipment code from a first smartcard in a smartcard reader, and obtaining a second equipment code from a memory location. The method further comprises determining whether the first equipment code matches the second equipment code, and, if a match is found, reading control instructions from the first smartcard and controlling a medical device according to the control instructions.

Still other objects of the present invention will become apparent to those skilled in this art from the following description wherein there is shown and described a preferred embodiment of this invention, simply by way of illustration, of a best mode contemplated for carrying out the invention. As will be realized, the invention is capable of other different aspects without departing from the scope of the invention. Accordingly, the drawings and description should be regarded as illustrative in nature and not as restrictive.

BRIEF DESCRIPTION OF THE DRAWINGS

While the specification concludes with claims particularly pointing out and distinctly claiming the invention, it is believed that the same will be better understood from the following description taken in conjunction with the accompanying drawings in which:

FIG. 4, starting with FIG. 4a and continuing to FIG. 4b, is a flow diagram depicting one method for secure data acquisition and control of portable medical equipment, according to the present invention.

DETAILED DESCRIPTION OF THE PREFERRED EMBODIMENTS

Figure 1:
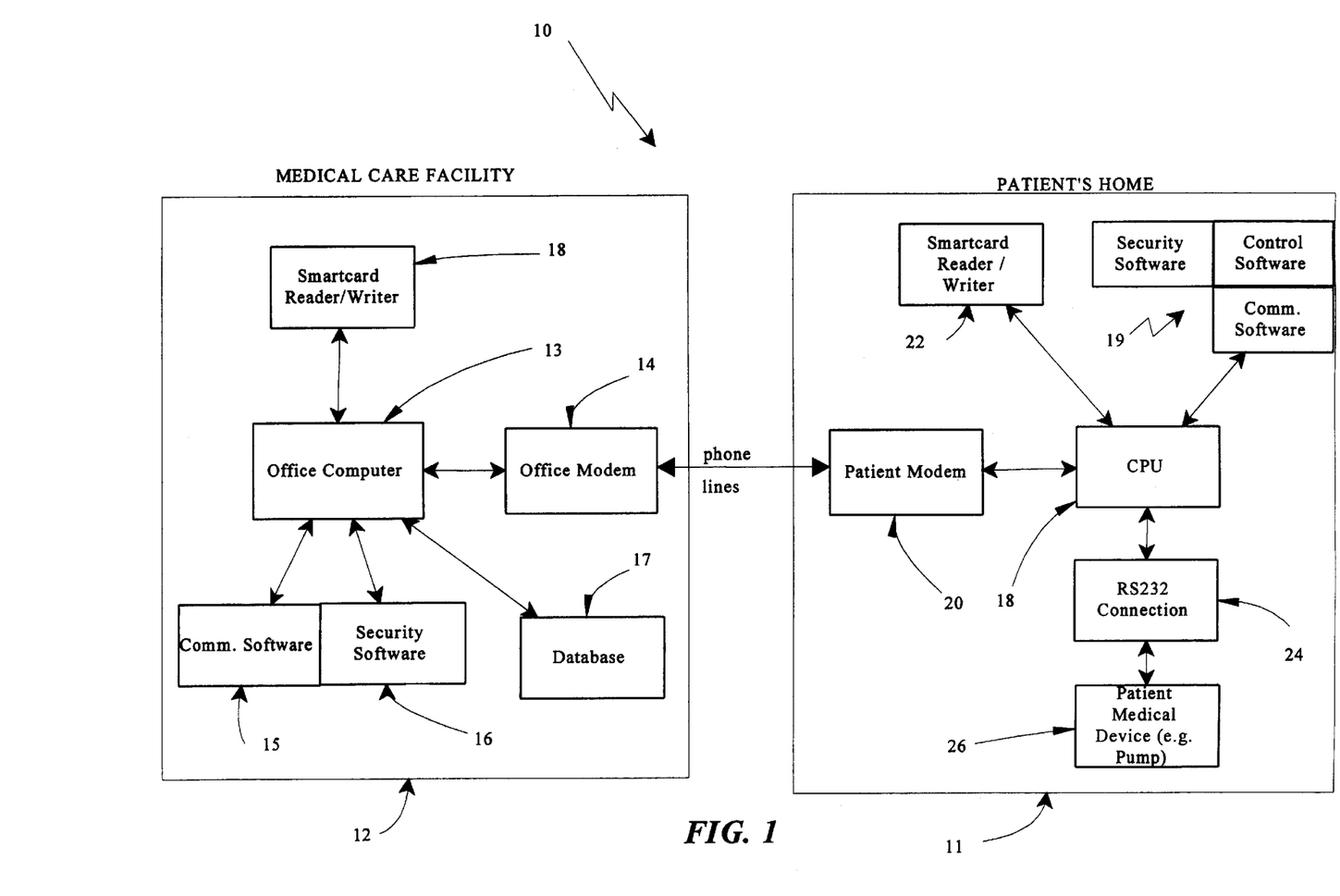
FIG. 1 is a block diagram illustrating a secure system according to the present invention for remote control of a pump located in a patient's home from a remote medical care facility, and for gathering data from the pump.

Referring now to the figures in detail, wherein like numerals indicate the same elements throughout the views, FIG. 1 illustrates a preferred embodiment of the present invention in the form of a secure remote control system 10 which allows a medicament dispensing patient pump or other medical device 26, located in a patient's home 11, to be controlled and monitored from a remote location, such as a medical care facility 12. The pump 26 delivers prescription medicine and/or other substances to the patient in a controlled manner in accordance with the medical treatment prescribed for the patient.

A modem 20 is located in the patient's home or other remote care area 11, for communicating with the modem 14 and computer 13 at the base medical care facility 12. A central processing unit (CPU) 18 controls the modem 20, as well as the smartcard reader/writer 22, and the pump 26. The CPU can be a standard microprocessor or microcontroller or other control unit which allows for communication as well as the execution of instructions. Software (and/or firmware) 19 is also provided in a memory unit for instructing the CPU with respect to the functions of communication, pump control, and security. Any of a variety of software routines can be utilized to enable the CPU to control the modem 20, and to, therefore, communicate with the modem 14 at the medical care facility 12. For example, the modem 20 might preferably include an "intelligent" modem, which can place voice communications on hold while the CPU is permitted to communicate.

The pump 26 delivers medicine or other substances to the patient and can include a pumping mechanism and a fluid reservoir which are interconnected. One pump which can be used includes a rotating camshaft which engages two reciprocating valves and a reciprocating expulser, such as, for example, the pumps disclosed in U.S. Pat. No. 5,338,157, issued to Blomquist. The valves and expulser engage a tube which is interconnected between the fluid reservoir and the patient. The rotating camshaft moves the valves and expulser to pump fluid from the reservoir through the tube and into the patient. Other drug delivery pumps and devices could be used as well, such as the VERIFUSE PLUS™ delivery system marketed by the I-Flow Corporation of Lake Forest, Calif.

While the preferred embodiment of FIG. 1 includes a drug delivery pump 26, it should be understood that this device could be any of a number of remotely located medical devices for which remote control and monitoring may be desire. For example, the system of FIG. 1 could be used to remotely control and monitor an oxygen delivery system, a pill dispenser, a respirator, a cardiograph, or other machine for use in home health care. While the term "pump" is utilized, it should be understood that pump 26 can equally be any of such medical devices.

Control software is provided with the software 19 for allowing the CPU 18 to control the pump 26 in the desired manner, and thereby enable the pump to deliver medicine or other substances to the patient in a controlled manner and in accordance with a medical treatment plan. For example, with a device for delivering fluid medicaments, the program would preferably comprise a number of algorithms and routines which control the rate at which the fluid is delivered to the patient, the frequency of administration of the fluid, the number of doses to be delivered, and other variables associated with drug delivery. For connection of the CPU 18 to the pump 26, an RS232 serial cable 24 can be used. Many common pumps have an external serial port for connection to a controller, such as CPU 18, and, therefore, the use of a serial connection is preferred. However, it is contemplated that a number of various connections and/or communication mechanisms can be used to allow the CPU 18 to communicate with the pump 26 as appropriate. For example, a wireless connection could be made between the two devices, such as by using radio frequency (RF) or infrared communications. Microcontrollers and associated programs for controlling drug delivery pumps and devices are disclosed in U.S. Pat. No. 5,338,157, the entire disclosure of which is incorporated herein by reference.

A smartcard reader/writer 22 is connected to the CPU 18 for control of the pump 26 and for gathering data from the pump. The smartcard reader/writer 22 should be capable of reading "smartcards", and/or other EEPROM (electrically erasable programmable read only memory) types of memory cards which can contain several thousand bytes of data, but typically can contain at least 32 bytes of memory. (A smartcard is typically a plastic card, usually about the size of a credit card, having a built in integrated circuit which provides a degree of logic, intelligence, and memory.) The smartcard reader/writer 22 is also preferably capable of writing data to the cards as well as reading the data, and can comprise any of a number of types of smartcard readers/writers known in the art, or other similar data reading devices. It is also contemplated that other types of cards and card readers could be used, such as magnetic cards and magnetic card readers, for example. Accordingly, as used herein the term "card" refers to any portable memory, logic device, or control media that can be conveniently carried by a person, such as in a wallet for example, and which can have data and/or instructions encoded thereon. For example, the term could encompass a variety of computer chips and bar codes.

In the system of FIG. 1, the pump control program works in conjunction with a prescription encoded on a patient smartcard. To read the smartcard, the card is placed within card reader/writer 22, as is known in the art. The patient's prescription is extracted from the patient smartcard and used by the control program to control the rate and frequency and/or other parameters of the drug administration, or other medical/therapy treatment.

In this way, the patient can carry his prescription with him or her in an easily transportable fashion, and can use it with other machines or medical devices situated in locations other than the patient's home. Moreover, the portable smartcard simplifies the programming process when the patient uses a different machine. Rather than having to reprogram the new machine, the patient can simply insert his or her smartcard and allow the prescription encoded on the smartcard to appropriately control the device. This eliminates the uncertainty, time and expense previously required for patients and health care providers to learn how to program different machines so that the desired prescription is delivered.

The prescription would preferably be encoded on the patient smartcard when the card is initialized by using a smartcard writer device, as described below with respect to FIG. 2. Thus, the patient prescription on the smartcard can be easily carried with the patient at all times, and can be used quickly and easily with other machines, if necessary or desirable. As used herein, the term "prescription" refers to the operational parameters, programs, or instructions for the medical device, such as the therapy regime, treatment protocol, dosing regime or therapy application, for example.

It is also contemplated that the pump may have its own internal controller for controlling implementation of drug delivery, dispensing or other treatment or therapy via the medical device. In this alternative example, CPU 18 is used to communicate and control the modem 20 and the smartcard reader/writer 22, and to control the internal pump controller through the connection 24 according to the program on the smartcard. It is further contemplated that the CPU (or controller), the modem, the software and the cardreader, can be combined as one integrated unit. The pump could also be included in such an integrated unit.

The patient smartcard can also be used to store data regarding the pump operation. For example, the CPU 18 can keep track of the data associated with the delivery of medicine to the patient, such as how much medicine was delivered, the times at which the medicine was delivered, the type of medicine which was delivered, any errors or warnings which occurred during delivery, and similar data. This data can be saved to the patient smartcard in the reader/writer 22, for ease of transportation by the patient and for paperless record keeping of the pump data. As is known, the smartcard is of a size which can be easily carried in the patient's wallet or purse. Moreover, the smartcard can withstand exposure to a variety of forces, temperatures, and substances while retaining the data and/or instructions encoded thereon Included with software 19 is security software, for ensuring that only authorized patients and/or health care providers are using the pump 26 (or other medical device connected to the CPU 18). As described in more detail below with respect to FIG. 3, the security software will not enable or disable the machine if the patient smartcard is not entered into the reader/writer 22, or if the patient smartcard is not encoded with the correct code for use with the particular machine which is connected. Thus, only individuals with an authorized smartcard can use the particular pump or device connected to the CPU 18.

At the medical care facility 12, there is provided a computer 13 which allows for remote communication with and control of the patient pump 26. The computer 13 can be a personal computer, notebook computer, or other control device capable of communicating data and instructions to and from a remote location. The computer 13 is also capable of running a variety of software programs, accessing databases, and controlling peripheral devices, as is known in the art.

In the illustrated example, connected to the computer is a modem 14 which allows the computer to communicate with the patient modem 20 over a telephone line. Communications software 15 connected to the computer 13 (preferably stored in the computer memory) allows the computer to control the modem 14 such that communication with the patient modem 20 can be achieved. The software 15 allows for the downloading of instructions, commands, and data, as well as the uploading of instructions, commands, and data, as is known in the art, and can utilize any of a variety of routines, algorithms, and protocols to achieve the desired communication. It is contemplated that other communication systems and mechanisms can be utilized to allow the computer 13 to communicate with the patient modem 20, other than the telephone line modems depicted in FIG. 1. For example, wireless communications systems, such as those using satellite communications or cellular communications, can be utilized.

The computer 13 also utilizes security software 16 to ensure that only authorized medical care providers can access and control the patient pump 26 from a remote location (e.g. 12). As described in farther detail below with respect to FIG. 4, the security software 16 reads an identification code from the provider smartcard which has been inserted into smartcard reader/writer 18 and compares this code to a list of authorized codes stored in the database 17. If the provider identification code matches one of the codes in the database 17, then the provider will be permitted to use the communication software 15 to dial into the patient modem 20 and CPU 18, and to thereby control and monitor the pump 26. If no such match exists, the provider will be denied access to the communication software 15.

Moreover, once the connection is made between computer 13 and CPU 18 using modems 14 and 20, the security software 16 downloads a provider code from the patient smartcard located in reader/writer 22. The provider code on the patient smartcard is compared with the provider identification code on the provider smartcard (located in reader/writer 22) to ensure that the two codes match. If no match is found, the connection is disabled and the provider cannot access the patient pump 26. (It should be noted that any means of verifying compatibility and authorization of the cards can be used. For example, a database or look-up table could be consulted to determine if a patient code from the patient card and a provider code from the provider card are compatible. Accordingly, whenever it is described herein that numbers or codes are "matched", it is to be understood that other means of determining compatibility can be used. Also, these codes can be automatically changed periodically by the computer 13 to prevent security breaches.)

However, if a match is found, the provider can perform a number of operations from the remote location 12. For example, and as described in further detail below, the provider can download the prescription information on the patient smartcard in the reader/writer 22. This prescription information can then be displayed on a monitor connected to the computer 13 and then edited using appropriate editing software provided with the computer. Any of a number of user interfaces and editing formats can be used to permit the editing of the prescription on the patient smartcard. Once the prescription is edited, it can then be uploaded back onto the patient smartcard, using the connection between modems 14 and 20. In this manner, the patient prescription can be appropriately modified and updated from remote location 12 without the need for the provider to visit the patient's home 11 (or bring the device into a base facility for service), and without the need for the provider to have a detailed knowledge of the operation of the pump 26. The provider need only know how to download and edit the prescription information on the patient smartcard located in the smartcard reader/writer 22.

In addition to allowing for the changing of prescription data on the patient smartcard, the remote control system depicted in FIG. 1 also allows other data to be downloaded from the patient location 11. For example, any data which is saved in the CPU 18, such as current settings of the pump 26 and current statuses of the pump, can be downloaded to the computer 13, viewed on the monitor, and saved into the database 17. In addition, historical data concerning pump operation can be downloaded from the patient smartcard in the smartcard reader/writer 22 and/or from the CPU 18, and then viewed and saved at the provider facility 12. This historical data can be compared to the prescription data on the patient smartcard and/or equipment specifications to ensure that the pump is operating properly. Other data associated with pump operation, such as that described in U.S. Pat. No. 5,338,157, can be downloaded and viewed by the provider from the medical care facility 12. Thus, the system of FIG. 1 allows the provider at the facility 12 to monitor pump operations remotely, and to quickly and easily obtain data regarding the pump operations.

Figure 2:
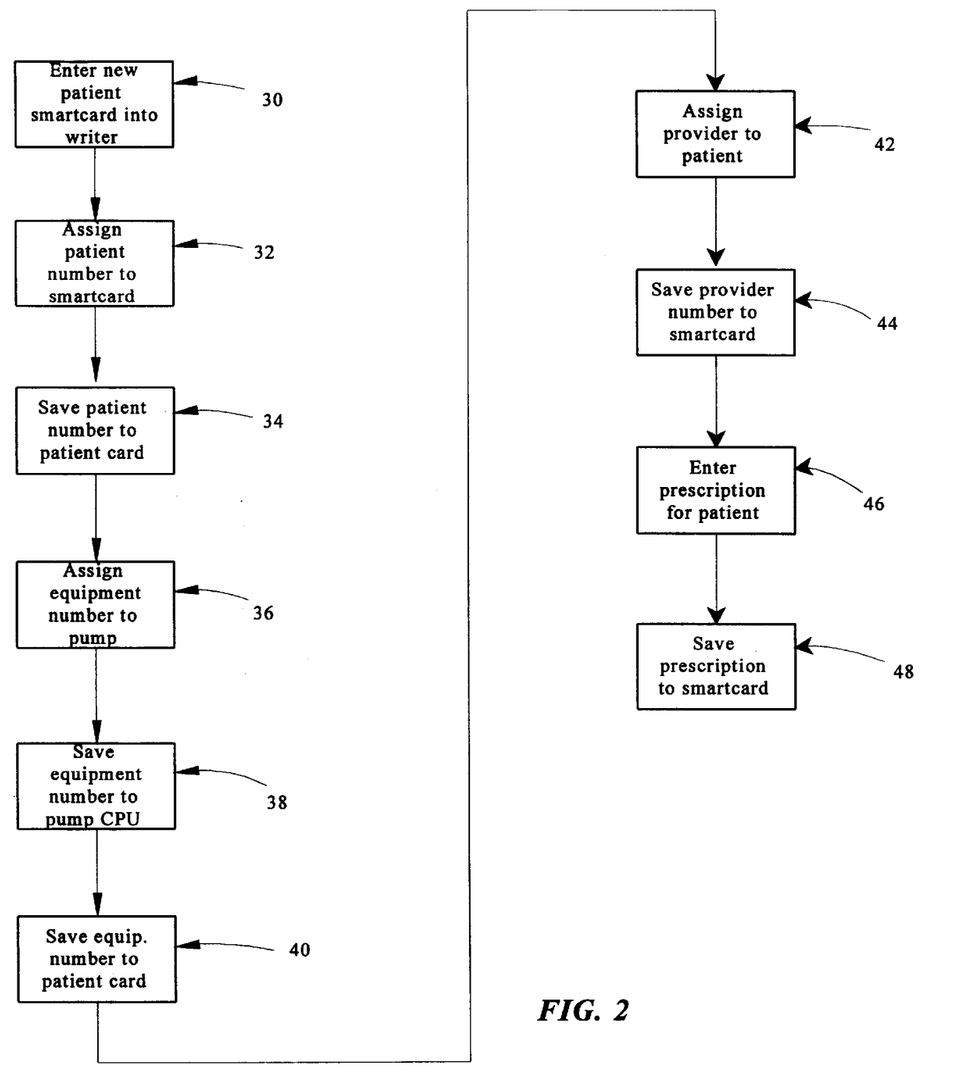
FIG. 2 is a flow diagram depicting a method according to the present invention for initialing exemplary smartcards and programs to be used with the device of FIG. 1, according to the present invention.

FIG. 2 is a flow diagram depicting a preferred method for initializing the provider and patient smartcards for use with the system of FIG. 1. At step 30, a new, uninitialized patient smartcard is entered into the smartcard reader/writer 18 at the medical care facility 12 of FIG. 1. Then, at step 32, a patient number is assigned to the patient, such as, for example, by using a patient tracking number program. Alternatively, the patient number can be assigned manually. Once assigned, the patient number is then saved to the smartcard, at step 34, such as in the conventional manner of saving data to a smartcard.

Then, at step 36, the piece of equipment (such as pump 26 of FIG. 1) to be used by the patient at the patient's home or other remote location is assigned a number. This number may correspond with the serial number on the equipment, or with an internal tracking number which has been assigned thereto. This equipment number is then saved to a memory location accessible by the CPU of the device, at step 38. Once the pump number has been assigned and saved to the CPU, the number is also saved to the patient smartcard, at step 40, such that the numbers on the patient smartcard and the in the pump CPU can be later matched by the security program provided with software 19 of FIG. 1, and described below with respect to FIG. 3.

Then, the patient is assigned to a health care provider or providers who will be primarily responsible for the patient during the home rehabilitation/treatment program. This occurs at step 42. The number for each provider, assigned earlier (e.g., an employee number), is then saved to the patient smartcard, at step 44. This number can be retrieved by the security program 16 of FIG. 1 for ensuring that only authorized providers treat the patient and access the pump control/data acquisition programs.

At step 46, the patients prescription is entered, such as by using a user interface with computer 13 of FIG. 1. This prescription information can include a variety of data, such as, for example, the type of drug to administer, the rate at which the drug should be administered, and the frequency of administration. Other data can also be entered at this time, such as the patient's medical history data, allergies and conditions, biographical information, and the like. Then, at step 48, all of the data is saved to the smartcard.

When saving the above described information to the patient smartcard, it should be ensured that the information is saved at the correct locations and/or in the correct formats. In this manner, future retrieval of the information is possible by a program or person who has knowledge of the saved data format, such as is known in the art of saving and retrieving data from smartcards.

Thus, the method depicted in FIG. 2 allows for the initialization/setup of the smartcards for use with the secure remote control/data acquisition system of FIG. 1. The entering of the described information and the saving of the information to the smartcards can be achieved using smartcard read/write/format programs, such as those developed and compatible with smartcard readers and writers.

Figure 3:
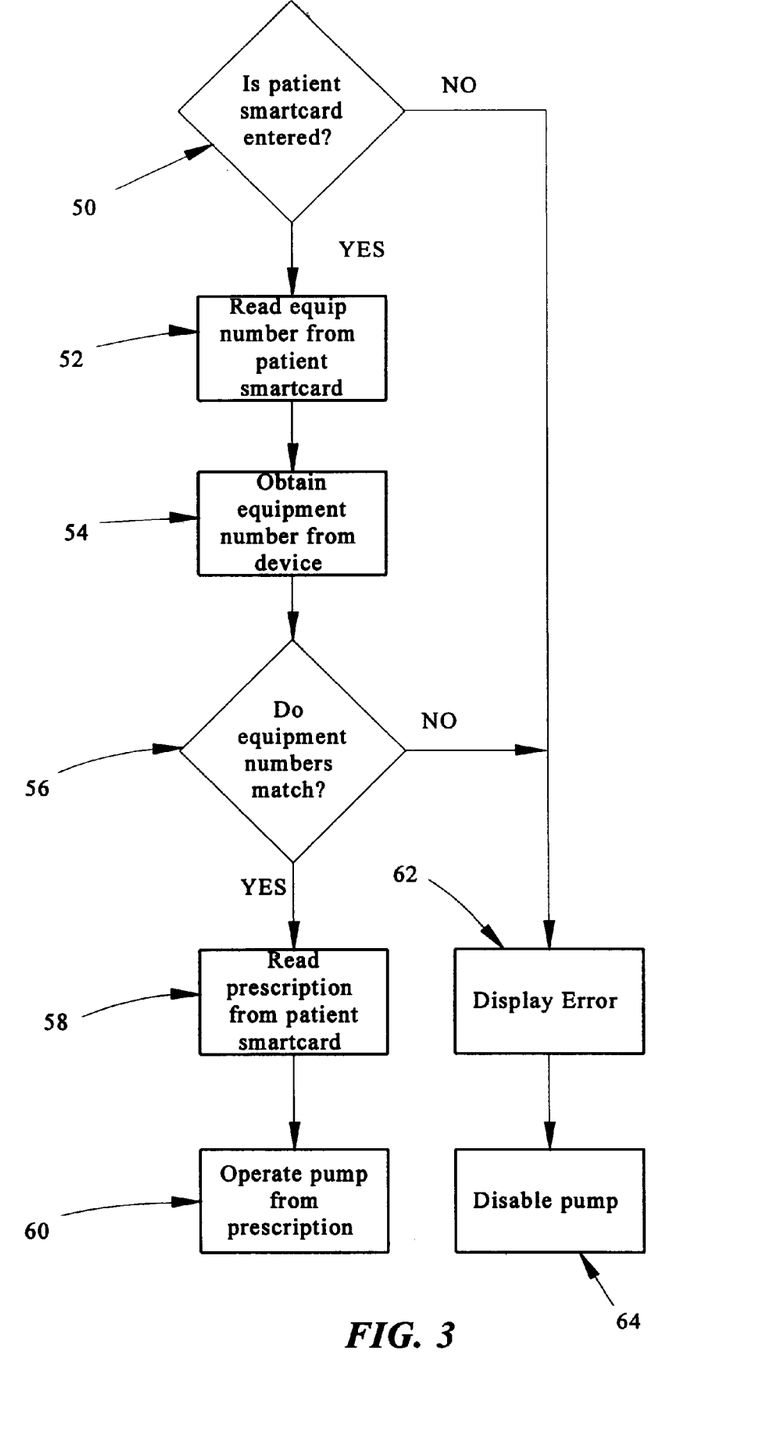
FIG. 3 is a flow diagram depicting a method according to the present invention for securely operating a portable medical device, such that only authorized patients can use the device.

FIG. 3 depicts the preferred operation of the security program located in software 19 of FIG. 1. The security program can be executed periodically to continually ensure that only authorized patients are using the pump, or other remote equipment located with the patient. According to the program, at step 50, it is determined whether the patient smartcard has been entered into the smartcard reader/writer 22. If no smartcard is entered into the reader (or the reader cannot otherwise read the card), operation of the pump should not be permitted, and, accordingly, an error signal is generated at step 62, and the pump is disabled or not enabled, at step 64.

If the smartcard has been entered into the reader, the method continues to step 52, and the equipment number (saved earlier to the patient smartcard, such as described with respect to the method of FIG. 2) is read from the patient smartcard by the smartcard reader/writer 22. Then, at step 54, the previously saved equipment number of the pump is obtained from memory located with the device or CPU. These two obtained numbers are then compared, at step 56, to determine if they match. If they do not match, an unauthorized patient card has been entered into the reader and the pump should not be permitted to operate. Accordingly, steps 62 and 64 are executed wherein an error message is displayed and the pump is disabled or not enabled. The pump may be disabled by sending a disabling signal to the pump, or the pump can be not enabled by simply not sending pump commands to the pump.

If, however, the equipment number on the patient card does match the equipment number stored with the device, step 58 is executed and the patient's prescription is read from the patient smartcard. This prescription data is then used, at step 60, to control the pump in the manner desired. The prescription data should be in the format required and expected by the pump or other device to be controlled. The particular format needed may vary depending upon the type of device which is to be controlled, as well as the communication protocol for the particular device.

Figure 4A:
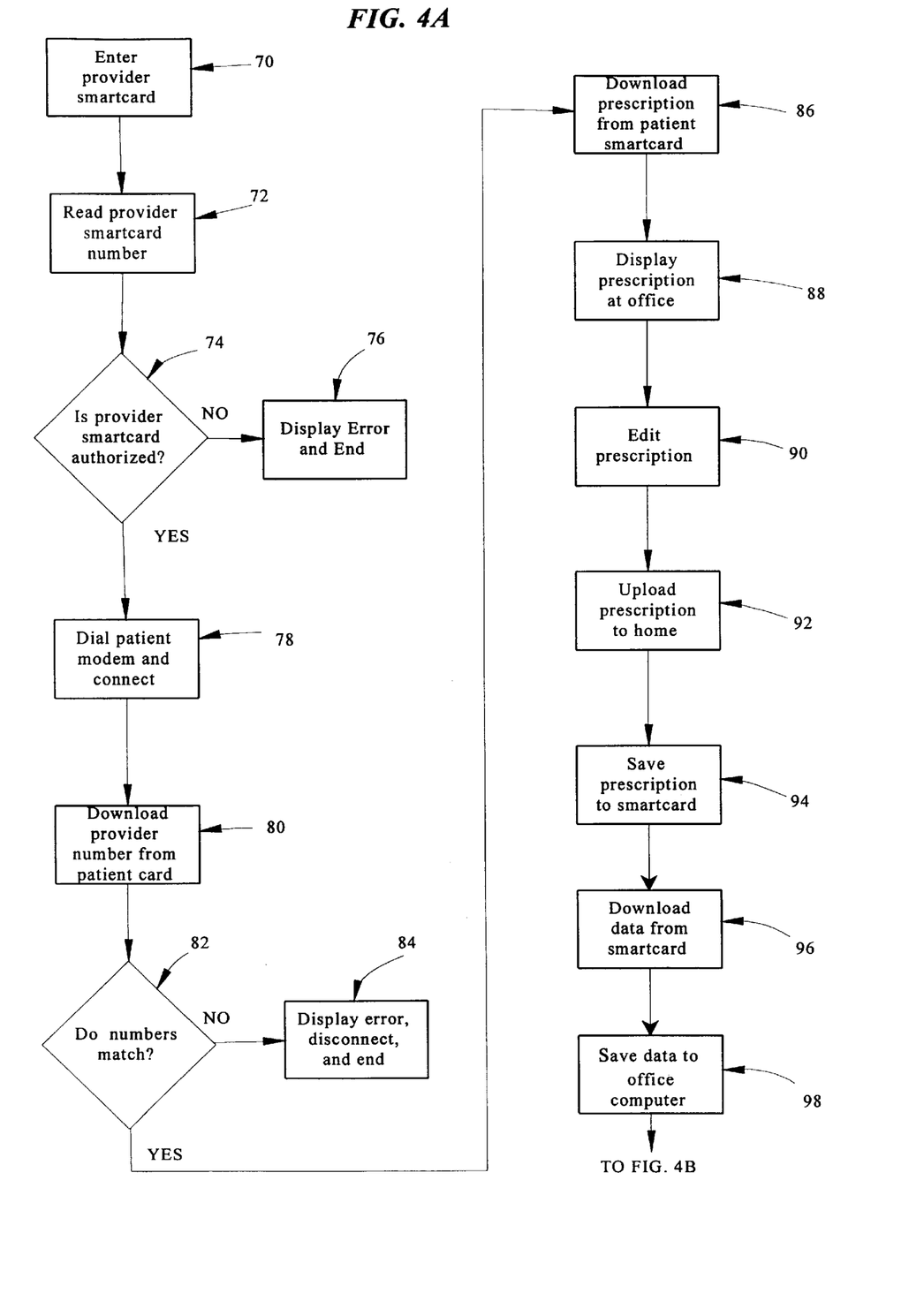
Figure 4B:
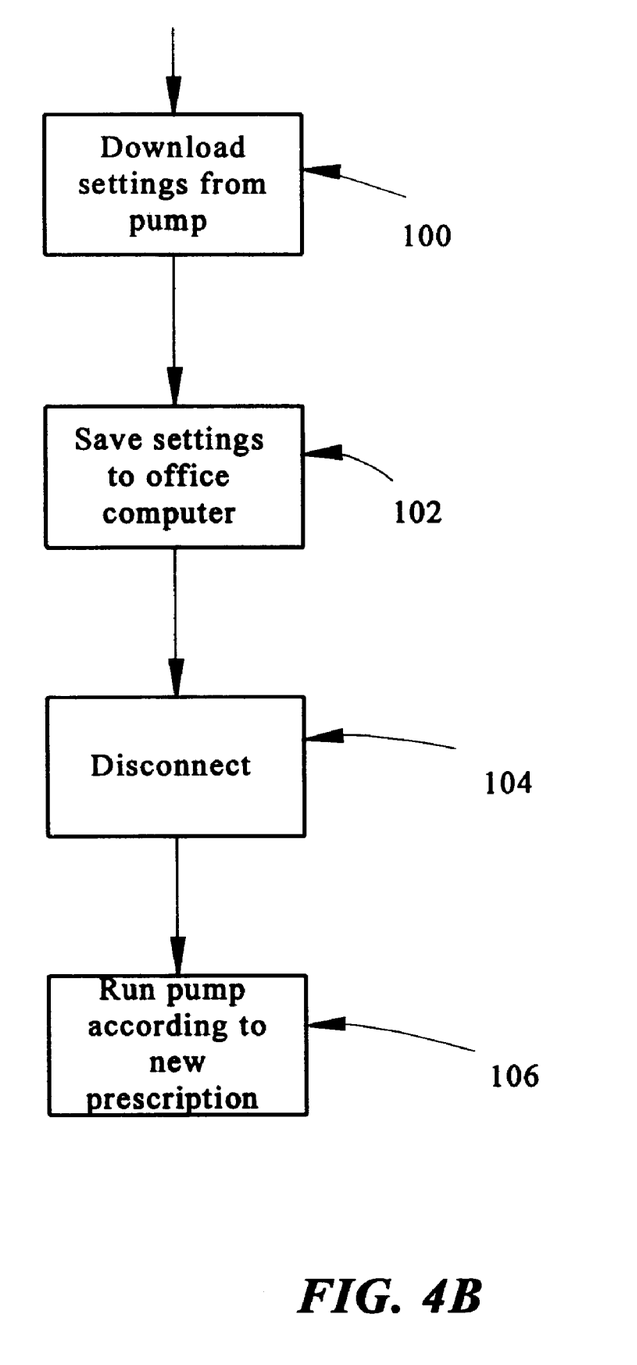

FIG. 4 (starting with FIG. 4a and continuing to FIG. 4b) is a flow diagram depicting a preferred method of operation for the security program 16 and communication program 15 of FIG. 1. (It should be noted that the two programs may be combined to operate as one algorithm if desired) According to this preferred method, the provider smartcard is entered into the reader 18, at step 70. The provider's number, which was previously encoded onto the provider smartcard, is read from the smartcard, at step 72. Then, at step 74, it is determined whether the provider number read from the smartcard matches an authorized code, i.e. it is determined whether the provider should be allowed to remotely access the patient pump 26. In the embodiment of FIG. 1, this can be attained by the computer 13 through a comparison of the provider number from the smartcard with a list of authorized provider numbers stored in database 17. If there is no match for the provider number which has been read, step 76 is executed wherein an error is displayed and the method is ended, thereby denying the provider access to the software for dialing in and remotely controlling the pump 26.

However, if there is a match for the provider number on the provider smartcard, step 78 is executed and the modem dials the phone number for the line connected to the patient's medical device. (This number can be selected by the provider from a list of phone numbers, or entered manually by the provider.) Once the connection has been established between the provider's computer and the controller of the remote device, the pump operation is put in standby or pause mode, and the program proceeds to download the provider number from the patient smartcard, at step 80 (i.e., the number of the provider authorized to treat the patient is downloaded). This number is compared, at step 82, to the provider number from the provider smartcard, previously read at step 72. If the numbers do not match, an error is displayed, the connection between the modems is terminated, and the program is ended, as shown at step 84.

However, if there is a match between the two numbers, step 86 is executed and the patient prescription is downloaded to the provider computer from the patient smartcard. This prescription can then be viewed at the provider computer (step 88) and edited by the provider (step 90) using appropriate data processing/editing means. Once the prescription has been edited, it can be uploaded back to the patient's smartcard, at step 92. It is then saved to the patient smartcard, at step 94, for future use and control of the patient pump.

In addition to allowing capabilities for secure modification of patient prescription data, the preferred method of FIG. 4 allows for data acquisition as well. More specifically, at step 96, pump operation data can be downloaded from the patient smartcard. This data is a record of the previous operations of the pump, and can indicate, for example, how much medicine has been delivered, when the medicine was delivered, and the rate of delivery. The data can be saved to the provider's computer, at step 98, for future reference, record keeping, and billing. In addition, the current pump settings can be retrieved from the pump, at step 100. These settings can include data corresponding to the most recent pump operations, as well as other data related to the pump, such as battery level, fluid levels, and the like. The settings can also be saved to the provider computer, at step 102.

When the prescription modification and data acquisition has been completed, the connection between the provider computer and the pump controller is disconnected, at step 104. The pump is then returned to normal operation mode and the newly edited prescription program, saved on the patient smartcard in the smartcard reader at the patient home, controls the pump in the programmed manner.

Thus, the preferred method of operation for the remote access program, depicted in the flow diagram of FIG. 4, allows only authorized care providers to access patient prescriptions and pump operation data. Moreover, the inventive method allows for the simple and efficient modification to the patient prescription by these authorized providers, and eliminates the need for a detailed knowledge of the patient's particular pump (or other medical device). In addition, the modifications can be made without the need for the provider to be physically present at the patient's home.

It should be understood that a program similar to that depicted in FIG. 4 can run on the pump controller at the patient home as well. Thus, when the provider does visit the patient, the provider can modify the patient prescription on site. The program preferably operates in a substantially similar manner to the method of FIG. 4, except that no modem connection would be necessary. The provider can carry a notebook computer or other portable controller along with a portable smartcard reader. Alternatively, the patient's smartcard reader can be used to read the patient and provider smartcards, one at a time, to ensure that the codes on each match. The pump operation data can be saved directly to the provider smartcard or to the computer/controller carried by the provider.

The methods depicted above are preferably embodied in computer programs that utilize input statements, output statements, decision statements, assignment statements, loops, variables, arrays, and/or other statements and techniques. For example, the "C" programming language or Visual Basic programming language could be utilized. As can be understood, such programs may take on a number of forms, utilize a variety of variable names and commands, and be implemented in any of a number of programming languages without departing from the scope of the invention.

While preferred exemplary embodiments of the present invention have been described, it is to be understood that further adaptions of the invention described herein can be accomplished by appropriate modifications by one of ordinary skill in the art without departing from the scope of the present invention. Accordingly, although preferred configurations of methods and devices embodying the present invention have been described, it is to be understood that these methods and devices may take on a wide variety of configurations and arrangements without departing from the scope of the present invention. For example, the steps of the methods discussed above may be practiced in a number of orders, without departing from the scope of the invention. Numerous alternatives have been mentioned herein, and other adaptions will become apparent to those skilled in the art. Therefore, the scope of the present invention should be considered in terms of the following claims and should not be limited to the details of the structures and methods shown and described in the specification and drawings.

What is claimed is:

1. A system for controlling a medical device, comprising:
    a medical device for use in medical treatment at a remote location, wherein the device is controllable by control instructions;
    a first portable card having control instructions encoded thereon;
    a first card reader for receiving the first portable card and for reading the control instructions from the first card;
    a control device in communication with the first card reader and the medical device, wherein the control device includes a control program for receiving the control instructions from the first card and applying the instructions to the medical device for control thereof;
    a first communication device connected to the control device, wherein the first communication device is controllable by the control device;
    a computer located at a distance from the remote location; and
    a second communication device connected to the computer, wherein the second communication device is controllable by the computer for communicating with the control device through the first communication device;
    wherein the computer is configured for receiving the control instructions from the first card through the communication devices, and for transmitting edited control instructions to the control device at the remote location, and wherein the control device is configured for saving the edited instructions to the first card in the first card reader.

2. The system as recited in claim 1, wherein the first card has a first provider code encoded thereon, and wherein the system further comprises:
    a second portable card having a second provider code encoded thereon;
    a second card reader connected to the computer for receiving the second portable card and for reading the second provider code therefrom; and
    wherein the computer includes a security program for receiving the first provider code and the second provider code and for disabling communication between the first and second communication devices if the codes are not compatible.

3. The system as recited in claim 1, further comprising:
    a second portable card having a provider code encoded thereon;
    a second card reader connected to the computer for receiving the second portable card and for reading the provider code therefrom; and
    wherein the computer includes a security program for receiving the provider code from the second card reader and comparing the code to a list of authorized provider codes stored in a memory, wherein the security program prevents communication between the first and second communication devices when the provider code does not match a code in the list.

4. A system for secure operation of a medical device, comprising:
    a medical device for use in medical treatment at a remote location, wherein the device is controllable by control instructions;
    a first portable card having a first code and control instructions encoded thereon;

a first card reader for receiving the first portable card and for reading the first code and control instructions from the first card;

a first control device in communication with the first card reader and the medical device, wherein the first control device includes a control program for applying the control instructions to the medical device for control thereof, a second control device located a distance from the remote location;

a communication system for allowing communication between the first control device and the second control device, wherein the second control device is configured to download the control instructions from the first card through the communication system and to allow editing of the downloaded instructions;

a second portable card having a second code encoded thereon;

a second card reader connected to the second control device for receiving the second portable card; and a first security mechanism in communication with the card readers for receiving the first and second codes from the cards, wherein the first security mechanism is configured to determine whether the codes are compatible and to prevent the editing of the control instructions if the codes are not compatible.

5. The system as recited in claim 4, further comprising a second security mechanism configured for preventing operation of the medical device when the first card cannot be read by the first card reader.

6. The system as recited in claim 4, wherein the first control device includes a security program for receiving a first device code from the first card and comparing the code to a second device code stored in a memory location, wherein the control device prevents operation of the medical device if the codes do not match.

7. The system as recited in claim 4, further comprising a user interface for allowing the editing of the control instructions.

8. The system as recited in claim 4, further comprising a second security mechanism for determining whether the second code matches a code in a database and for preventing communication between the control devices if no match is found.

9. A method for securely controlling a medical device using a smartcard and a smartcard reader, the method comprising:

reading a first equipment code from a first smartcard in a smartcard reader;

obtaining a second equipment code from a memory location;

determining whether the first equipment code matches the second equipment code;

if a match is found, reading control instructions from the first smartcard, and controlling a medical device according to the control instructions;

reading a first access code from the first smartcard;

reading a second access code from a second smartcard;

determining whether the access codes are compatible; and if compatibility is found, downloading the control instructions from the first smartcard to a remote location, editing the control instructions, and saving the edited control instructions to the first smartcard.

\* \* \* \* \*